United States Patent [19]
Roling

[11] Patent Number: 5,271,863
[45] Date of Patent: Dec. 21, 1993

[54] COMPOSITIONS FOR EXTRACTING IRON SPECIES FROM LIQUID HYDROCARBON SYSTEMS

[75] Inventor: Paul V. Roling, Spring, Tex.

[73] Assignee: Betz Laboratories, Inc., Trevose, Pa.

[21] Appl. No.: 841,690

[22] Filed: Feb. 26, 1992

[51] Int. Cl.$^5$ .............................................. C01B 31/16
[52] U.S. Cl. ................................................... 252/184
[58] Field of Search ........................ 252/182.12, 184

[56] References Cited

U.S. PATENT DOCUMENTS

| | | | |
|---|---|---|---|
| 3,355,270 | 11/1967 | Amick et al. | 44/367 |
| 3,703,473 | 11/1972 | Lasco | 252/184 |
| 4,105,690 | 8/1978 | Christidis et al. | 562/444 |
| 4,130,582 | 12/1978 | Petree et al. | 562/448 |
| 4,217,235 | 8/1980 | Karlsson | 252/184 |
| 4,749,468 | 6/1988 | Roling et al. | 208/48 AA |
| 4,847,415 | 7/1989 | Roling et al. | 252/182.12 |

*Primary Examiner*—Edward A. Miller
*Attorney, Agent, or Firm*—Alexander D. Ricci; Philip H. Von Neida

[57] ABSTRACT

Compositions and methods of extracting soluble iron species, such as iron naphthenate, from a liquid hydrocarbon, such as crude oil are disclosed. A Mannich reaction product is added to the liquid hydrocarbon and mixed therewith. Then, wash water is added to form a water-in-oil emulsion. The emulsion is resolved, with the iron laden aqueous phase being separated.

4 Claims, No Drawings

COMPOSITIONS FOR EXTRACTING IRON SPECIES FROM LIQUID HYDROCARBON SYSTEMS

FIELD OF THE INVENTION

The present invention pertains to compositions and methods for removing soluble iron specie contaminants from liquid hydrocarbon systems.

BACKGROUND OF THE INVENTION

Liquid hydrocarbon mediums, represented by crude oil and crude oil fractions such as naphtha, gasoline, kerosene, jet fuel, fuel oil, gas oil and vacuum residuals, often contain metal contaminants that, upon processing of the medium can catalyze undesirable decomposition of the medium or accumulate in the process residue. Accumulation of iron contaminants, like other metal contaminants, is undesirable in the product remaining after refinery, purification, or other processes and, accordingly diminishes the value of such products.

Similar iron contamination problems are experienced in conjunction with other liquid hydrocarbons, including aromatic hydrocarbons, such as benzene, toluene, and xylene; chlorinated hydrocarbons, such as ethylene dichloride, and olefinic and naphthenic process streams. All of the above petroleum feedstock, fractions and petrochemicals are referred to herein as "liquid hydrocarbonaceous mediums".

Iron in such liquid hydrocarbonaceous mediums may occur in a variety of forms. For example, it may be present as a naphthenate, porphyrin, or sulfide. In any case, its presence can be troublesome. An example of the problems of iron in hydrocarbons is the use of residuals of iron-containing crudes used to form graphite electrodes for industry. The value and useful life of these electrodes is diminished proportionately with the level of undesirable iron contamination.

Additionally, in many processes iron-containing catalysts are used which may carry over with the product during purification. Iron catalyst contaminated product leads to deleterious effects.

SUMMARY OF THE INVENTION

The present invention provides for compositions and methods of removing iron species from liquid hydrocarbonaceous medias. The hydrocarbonaceous medium is contacted with a Mannich reaction product which forms a complex with the iron species. Water is then added and an emulsion is formed. The iron laden water is subsequently removed from the emulsion after the emulsion has been separated.

DESCRIPTION OF THE RELATED ART

U.S. Pat. No. 4,749,468, Roling et al., June 1988, teaches methods for chelating and deactivating copper in hydrocarbon fluids. Certain Mannich reaction products are used to not only chelate and deactivate copper but also iron as well.

DETAILED DESCRIPTION OF THE INVENTION

The present invention provides for compositions and methods for extracting iron species from a liquid hydrocarbonaceous medium comprising contacting said medium with a Mannich reaction product to form a chelant containing reaction mixture, then adding water to said reaction mixture to form an emulsion, separating said emulsion and removing the iron laden water from said separated emulsion.

The Mannich reaction product is formed by reacting three components (A):(B):(C) comprising (A) para-alkyl phenol where the alkyl group can be methyl or ethyl, (B) an amine having the formula $H_2N-R-G$ where R is a 2 to 5 carbon alkylene group and G is hydrogen or methoxy, and (C) glyoxylic acid. The weight ratios of these three components ranges from 1:1:1 to 1:3:1.

The preferred Mannich reaction product is 3-methoxypropylamine-N-(2'-hydroxy-5'-methylphenylacetic acid) 3-methoxypropylamine salt (MMPA). This compound is prepared in the following fashion: In a 250-ml three-necked, round-bottomed flask, equipped with a Dean-Stark trap and condensor, a thermometer, a septum cap and magnetic stirrer, was placed 10.8 g (0.10 mole) of p-cresol (PC), 50 ml of xylene, and 17.8 g (0.20 mole) of 3-methoxypropylamine (MOPA). The mixture was heated to 82° C. with stirring. By means of a syringe pump, 11.0 ml (14.8 g, 0.10 mole) of a 50 wt % aqueous solution of glyoxylic acid (GA) was added over 2 hours. Temperature was maintained in the range of 78° to 92° C. during the addition period and for 2 hours afterward. Heat was then increased to 125° C. and 8.5 ml of water and 8.5 ml of xylene were collected in the trap. This results in 65.8 g (about 53% actives) of an orange-brown solution. The molar ratio of PC:MOPA:GA was 1:2:1.

The Mannich reaction product can be added to the liquid hydrocarbonaceous medium in an amount from about 1 to about 10 moles based upon each mole of iron present in the liquid hydrocarbon. The uniqueness of the present compounds is that they are soluble in both organic solvents and water. Preferably, these compounds are in an organic carrier solvent when added to the liquid hydrocarbon which is to be treated.

The compounds of the present invention can be fed neat to the hydrocarbon or, dissolved or dispersed in an organic solvent, such as heavy aromatic naphtha (HAN), glyme, diglyme, triglyme, methyl alcohol, benzene, xylene, hexane, etc., for direct introduction into the liquid hydrocarbonaceous medium. Preferably, the Mannich reaction product is dissolved in a polar organic solvent such as HAN or xylene.

After the chelant is added to and mixed with the liquid hydrocarbon, water is added to the resulting mixture of hydrocarbon-chelant in an amount of about 1–15% water based on the weight of the liquid hydrocarbon. Preferably, water is added in an amount of about 5–10 wt.%. The water/oil emulsion thus formed is resolved with iron laden aqueous phase being separated. Reduced iron content hydrocarbon phase may be then subjected to further processing prior to end-use or it may be directly used for its intended end purpose as a fuel, etc.

Preferably, the emulsion is resolved in a conventional desalter apparatus. In typical desalters, optional pH operating conditions are maintained at from about 6–10 in order to retard corrosion and enhance emulsion resolution. Conventional desalters also utilize heat treatment and electric fields to aid in emulsion resolution. The methods of the present invention provide improvement in iron removal at such operating pH's and under the treatment conditions normally encountered in desalters.

The present invention has demonstrated effective removal of both iron naphthenate species from xylene and is therefore expected to function well with a host of liquid hydrocarbons and iron contaminants.

At present, a solution with up to 53% actives can be employed, however, the preferred solution comprises about 25% of the MMPA compound dissolved in HAN.

Although the invention has been generally described for use in conjunction with petroleum crudes, other environments are contemplated. In fact, the present invention is thought applicable to extraction of iron from any iron containing liquid hydrocarbon. For example, in the manufacture of ethylene dichloride (EDC), hydrocarbon ethylene is chlorinated with the use of an iron containing catalyst. Carryover of the iron containing catalyst with the desired product during product purification diminishes the value and performance of the ethylene dichloride. Extraction of the liquid ethylene dichloride with the Mannich product in accordance with the invention will reduce such contamination.

The invention will now be further described with reference to a number of specific examples which are to be regarded solely as illustrative, and not as restricting the scope of the invention.

EXAMPLES

In order to access the efficacy of the invention in extracting iron species from liquid hydrocarbons, the following examples were undertaken.

PROCEDURE

In a separatory funnel was placed 95 mL of a 0.001 M (95 umol or 56 ppm) iron naphthenate (FeN) in xylene solution. This solution was heated to 75±5 deg C. and an appropriate amount of the preparation above added. The solution immediately turned deep purple. While maintaining the 75 deg C., 10 mL of de-ionized water was added and the mixture shaken, then allowed to separate. Some "solids" would form on the walls of the funnel and these were gently agitated to move into the water layer. The water layer was deep purple, while the xylene layer was light purple. The xylene layer was then extracted with concentrated hydrochloric acid three times with 10 mL, 10 mL, and 5 mL portions.

The water layer was acidified with 5 mL of concentrated hydrochloric acid to destroy the purple complex, which otherwise led to low iron balances. An aliquot of the water layer (0.50 mL) was treated with 0.040 mL of 3% hydrogen peroxide, 3.0 mL of a saturated aqueous ammonium thiocyanate solution, 4.0 mL of concentrated hydrochloric acid and diluted to 100 mL with deionized water. The percent transmittance of this solution in 2.5 cm cells was determined and the umols of iron calculated by the equation:

umols Fe =

$$\frac{\text{mL of water used in the Extraction} \times (A - 0.0315) \times 4.71}{\text{mL of water used in Fe test}}$$

where A is the absorbance and the numbers were determined from a standard curve.

A commercial iron standard of 1000 ppm was diluted to 56 ppm and used to generate a standardized line for use in the above equation.

The combined hydrochloric acid extracts were similarly worked up to yield the umols of iron left in the xylene layer. The extraction was acceptable when the iron balance, the sum of the umols of iron in the water and in the xylene layer, was within 95±15. Three runs where the purple complex in the water layer was not destroyed with the 5 mL of concentrated hydrochloric acid gave iron balances of 75, 71, and 58.

Conditions and results of iron extractions with the above salt are listed in Table I. The data show that this salt extracts iron effectively, especially when added to the hydrocarbon layer at elevated temperatures.

TABLE I

Extraction of Iron Naphthenate from Xylene to Water Utilizing MMPA

| umols Fe used | Temp °C. | umol Treatment | ml H$_2$O in Extr. | Umols Fe Remove(a) | % Fe Removed | Fe Balance |
|---|---|---|---|---|---|---|
| 95 | 75 | 731 | 10 | 91 | 85 | 107 |
| 95 | 75 | 365 | 10 | 88 | 83 | 106 |
| 95 | 75 | 146 | 10 | 62 | 63 | 99 |
| 95 | 75 | 73 | 10 | 24 | 26 | 92 |
| 95 | 20 | 146 | 10 | 26 | 25 | 104 |
| 95 | 75 | 146 | 5 | 52 | 50 | 105 |
| 95 | 75 | 175(b) | 5 | 58 | 61 | 104 |
| 95 | 95 | 146 | 5 | 54 | 49 | 110 |
| 95 | 75 | 146(c) | 5 | 19 | 18 | 108 |
| 18 | 75 | 29 | 10 | 8 | 42 | 19 |
| 95 | 75 | 0 | 5 | 8 | 9 | 87 |

(a) umols of iron based on a total of 95 umols
(b) new preparation of this material
(c) treatment added to the 5 ml of water before mixing with the xylene
MMPA = 3-methoxypropylamine-N-(2'-hydroxy-5'-methylphenylacetic acid)3-methoxypropylamine salt As seen in Table I, the compounds of the present invention prove effective at removing iron specie from hydrocarbon liquids.

TABLE II

Extractions of 95 umol of iron naphthenate from xylene to water (5.0 ml water at 75° C.)

| Treatment (pH:Amine:GA Molar Ratio) | umol Treatment | umols Fe Removed | % Fe Removed | Fe Balance |
|---|---|---|---|---|
| PC:MOPA:GA (1:1:1) | 220 | 17 | 17 | 103 |
| PC:MOPA:GA (1:1:1) + MOPA (1) | 220 | 11 | 11 | 105 |
| PC:t-amylamine:GA (1:2:1) | 180 | 18 | 18 | 103 |
| p-t-butylphenol:MOPA:GA (1:2:1) | 170 | 7 | 7 | 98 |
| pc:M-600:GA (1:1:1) | 330 | 5 | 5 | 112 |

MOPA is 3 methoxypropylamine
PC is p-cresol
GA is glyoxylic acid

As seen in Table II, differing molar ratios still proved effective at iron extraction. MOPA and t-amylamine proved to be effective starting ingredients while t-butylphenol and Jeffamine M-600 compound did not prove effective.

While this invention has been described with respect to particular embodiments thereof, it is apparent that numerous other forms and modifications will be obvious to those skilled in the art. The appended claims generally should be construed to cover all such obvious forms and modifications which are within the true spirit and scope of the present invention.

Having thus described the invention, what I claim is:

1. An iron extracting composition comprising a liquid hydrocarbon and a Mannich reaction product formed by reacting three components (A):(B):(C) comprising (A) a para-alkyl phenol where the alkyl is methyl or ethyl (B) an amine having the formula H$_2$N—R—G where R is a 2 to 5 carbon alkylene group and G is hydrogen or methoxy and (C) glyoxylic acid.

2. The composition as claimed in claim 1 wherein said Mannich reaction product is 3-methoxypropylamine-N-(2'-hydroxy-5'-methylphenylacetic acid) 3-methoxypropylamine salt.

3. The composition as claimed in claim 1 wherein said liquid hydrocarbon is selected from the group consisting of heavy aromatic naphtha or xylene.

4. The composition as claimed in claim 1 wherein said Mannich reaction product is soluble in a dual organic-/aqueous medium.

* * * * *